United States Patent
Myoung et al.

(10) Patent No.: US 11,173,108 B2
(45) Date of Patent: Nov. 16, 2021

(54) SKIN WHITENING COMPOSITION COMPRISING CULTURED PRODUCT OF PSEUDOALTEROMONAS PEPTIDOLYTICA OR EXTRACT THEREOF

(71) Applicant: Amorepacific Corporation, Seoul (KR)

(72) Inventors: Kilsun Myoung, Yongin-si (KR); Jaeyoung Ko, Yongin-si (KR); Yong Jin Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 16/647,295

(22) PCT Filed: Sep. 14, 2018

(86) PCT No.: PCT/KR2018/010834
§ 371 (c)(1),
(2) Date: Mar. 13, 2020

(87) PCT Pub. No.: WO2019/054794
PCT Pub. Date: Mar. 21, 2019

(65) Prior Publication Data
US 2020/0214972 A1    Jul. 9, 2020

(30) Foreign Application Priority Data
Sep. 15, 2017 (KR) .......................... 10-2017-0118927

(51) Int. Cl.
*A61K 35/74* (2015.01)
*A61K 8/99* (2017.01)
(Continued)

(52) U.S. Cl.
CPC ................ *A61K 8/99* (2013.01); *A61Q 19/02* (2013.01); *C12N 1/20* (2013.01); *C12N 1/205* (2021.05); *C12R 2001/01* (2021.05)

(58) Field of Classification Search
CPC ...................................................... A61K 35/74
See application file for complete search history.

(56) References Cited

U.S. PATENT DOCUMENTS

| 7,022,668 B2 | 4/2006 | Duena et al. |
| 8,420,355 B2 | 4/2013 | Genicot et al. |
| (Continued) | | |

FOREIGN PATENT DOCUMENTS

| CN | 105950590 B | 7/2019 |
| JP | 4252444 B2 | 4/2009 |
| (Continued) | | |

OTHER PUBLICATIONS

Blast2 alignment of Seq ID No. 1 and the 16S rRNA sequence of Pseudoalteromonas strain No. J021 of Tebben et al., NCBI web site, https://blast.ncbi.nlm.nih.gov/Blast.cgi?PAGE=MegaBlast &PROGRAM=blastn&BLAST_PROGRAMS=megaBlast&PAGE_TYPE=BlastSearch&BLAST_SPEC=blast2seq&DATABASE=n/a &QUERY=&SUBJECTS=, Apr. 19, 2021.*
(Continued)

*Primary Examiner* — Rosanne Kosson
(74) *Attorney, Agent, or Firm* — Sughrue Mion, PLLC

(57) ABSTRACT

Disclosed in the present specification is a skin whitening composition comprising a *Pseudoalteromonas peptidolytica* strain, a lysate thereof, a cultured product thereof or an extract of the strain, lysate or cultured product as an active ingredient. Disclosed in the present specification is a *Pseudoalteromonas peptidolytica* strain SNC 130, having an accession number of KCCM12050P, which has a skin whitening function.

7 Claims, 3 Drawing Sheets
Specification includes a Sequence Listing.

(51) Int. Cl.
    *A61Q 19/02*     (2006.01)
    *C12N 1/20*     (2006.01)
    *C12R 1/01*     (2006.01)

(56) References Cited

U.S. PATENT DOCUMENTS

| 2011/0195103 A1 | 8/2011 | Areas et al. |
| 2017/0333491 A1 | 11/2017 | Soley Astals et al. |

FOREIGN PATENT DOCUMENTS

| KR | 10-0784486 B1 | 12/2007 |
| KR | 10-0812922 B1 | 3/2008 |
| KR | 10-2010-0109743 A | 10/2010 |
| KR | 10-2012-0068367 A | 6/2012 |
| KR | 10-2014-0024840 A | 3/2014 |
| KR | 10-2016-0126204 A | 11/2016 |
| KR | 10-2016-0146112 A | 12/2016 |
| KR | 101686399 B1 | 12/2016 |
| KR | 1020170072341 A | 6/2017 |
| WO | 2008/084890 A1 | 7/2008 |
| WO | 2009/106343 A1 | 9/2009 |
| WO | 2012/072245 A2 | 6/2012 |
| WO | 2016/001551 A1 | 1/2016 |

OTHER PUBLICATIONS

Jan Tebben, et al., "Induction of Larval Metamorphosis of the Coral Acropora millepora by Tetrabromopyrrole Isolated from a Pseudoalteromonas Bacterium", PLoS ONE, Apr. 2011, pp. 1-8, vol. 6, No. 4.

John P. Bowman, "Bioactive Compound Synthetic Capacity and Ecological Significance of Marine Bacterial Genus *Pseudoalteromonas*", Marine Drugs, 2007, pp. 220-241, vol. 5.

Kasthuri Venkateswaran, et al., "*Pseudoalteromonas peptidolytica* sp. nov., a novel marine mussel-thread-degrading bacterium isolated from the Sea of Japan", International Journal of Systematic and Evolutionary Microbiology, 2000, pp. 565-574, vol. 50.

GenBank: AB680359.1: Pseudoalteromonas carrageenovora gene for 16S rRNA, partial sequence, strain NBRC 12985 (Jan. 28, 2012).

Won-Jae Chi, et al., "Isolation and Characterization of an Agar-hydrolyzing Marine Bacterium, *Pseudoalteromonas* sp. H9, from the Coastal Seawater of the West Sea, South Korea", Microbiology and Biotechnology Letters, 2015, pp. 134-141, vol. 43, No. 2.

International Search Report of PCT/KR2018/010834 dated Mar. 14, 2019 [PCT/ISA/210].

\* cited by examiner

[FIG. 1]

CATGCAGTCGAGCGGTAACATTTCTAGCTTGCTAGAAGATGACGAGCGGCGGACGGGTG
AGTAATGCTTGGGAACATGCCTTGAGGTGGGGGACAACCATTGGAAACGATGGCTAATAC
CGCATAATGTCTACGGACCAAAGGGGGCTTCGGCTCTCGCCTTTAGATTGGCCCAAGTGG
GATTAGCTAGTTGGTGAGGTAAGGGCTCACCAAGGCGACGATCCCTAGCTGGTTTGAGAG
GATGATCAGCCACACTGGAACTGAGACACGGTCCAGACTCCTACGGGAGGCAGCAGTGGG
GAATATTGCACAATGGGCGCAAGCCTGATGCAGCCATGCCGCGTGTGTGAAGAAGGCCTT
AGGGTTGTAAAGCACTTTCAGTCAGGAGGAAAGGTTAGTAGTTAATACCTGCTAGCTGTG
ACGTTACTGACAGAAGAAGCACCGGCTAACTCCGTGCCAGCAGCCGCGGTAATACGGAGG
GTGCGAGCGTTAATCGGAATTACTGGGCGTAAAGCGTACGCAGGCGGTTTGTTAAGCGAG
ATGTGAAAGCCCCGGGCTTAACCTGGGAACTGCATTTCGAACTGGCAAACTAGAGTGTGA
TAGAGGGTGGTAGAATTTCAGGTGTAGCGGTGAAATGCGTAGAGATCTGAAGGAATACCG
ATGGCGAAGGCAGCCACCTGGGTCAACACTGACGCTCATGTACGAAAGCGTGGGGAGCAA
ACAGGATTAGATACCCTGGTAGTCCACGCCGTAAACGATGTCTACTAGGAGCTGGGGTCT
TCGGACAACTTTTCCAAAGCTAACGCATTAAGTAGACCGCCTGGGGAGTACGGCCGCAAG
GTTAAAACTCAAATGAATTGACGGGGGCCCGCACAAGCGGTGGAGCATGTGGTTTAATTC
GATGCAACGCGAAGAACCTTACCTACACTTGACATACAGAGAACTTACCAGAGATGGTTT
GGTGCCTTCGGGAACTCTGATACAGGTGCTGCATGGCTGTCGTCAGCTCGTGTTGTGAGA
TGTTGGGTTAAGTCCCGCAACGAGCGCAACCCCTATCCTTAGTTGCCAGCGATTCGGTCG
GGAACTCTAAGGAGACTGCCGGTGATAAACCGGAGGAAGGTGGGGACGACGTCAAGTCAT
CATGGCCCTTACGTGTAGGGCTACACACGTGCTACAATGGCAGGTACAGAGAGCAGCGAG
CTAGCGATAGTGAGCGAATCCCTTAAAGCCTGTCGTAGTCCGGATTGGAGTCTGCAACTC
GACTCCATGAAGTCGGAATCGCTAGTAATCGCGAATCAGAATGTCGCGGTGAATACGTTC
CCGGGCCTTGTACACACCGCCCGTCACACCATGGGAGTGGGTTGCTCCAGAAGTG (SEQ ID NO: 1)

[FIG. 2]
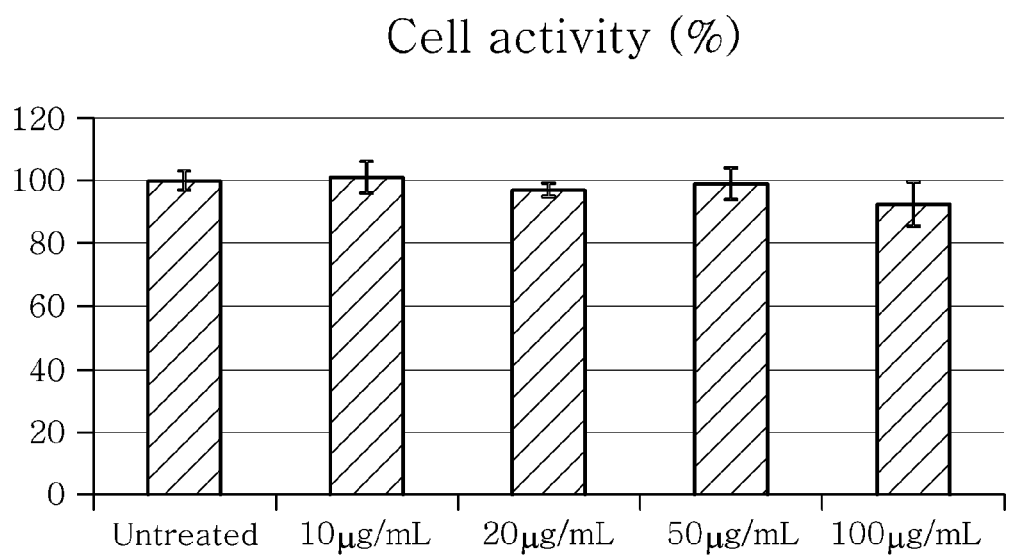
[FIG. 3]
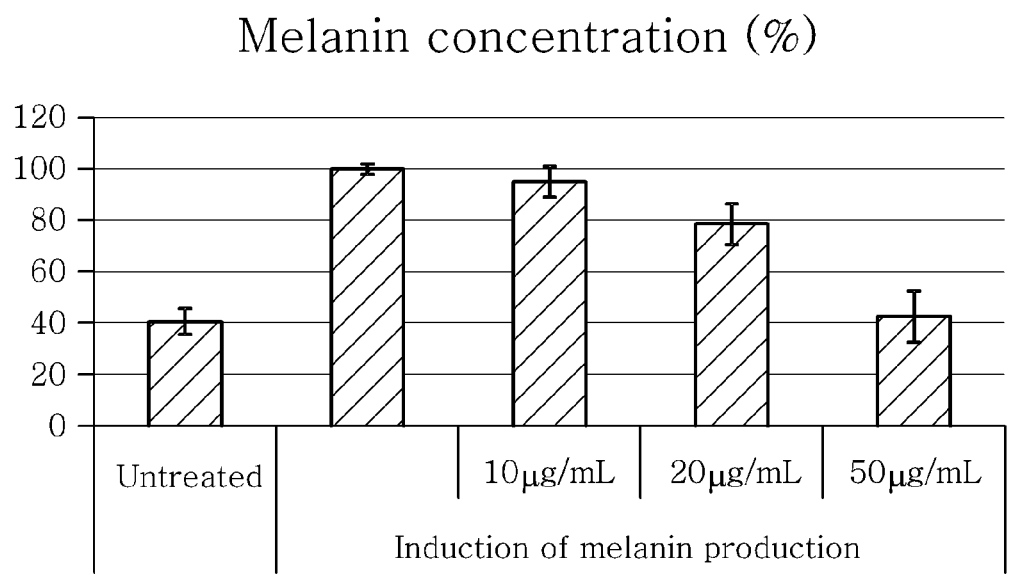

[FIG. 4]
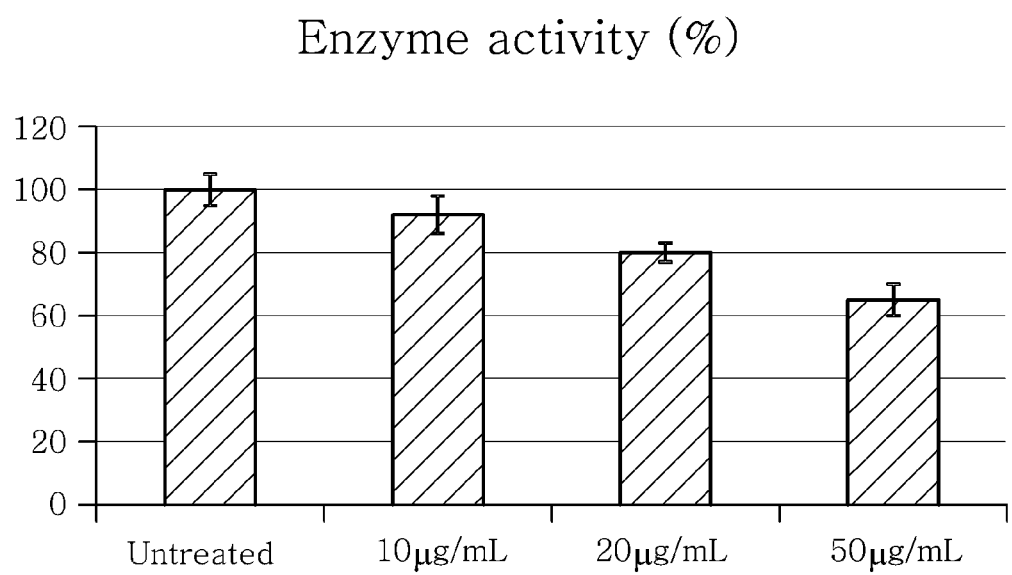

SEQUENCE LISTING

```
<160> NUMBER OF SEQ ID NOS: 3

<210> SEQ ID NO 1
<211> LENGTH: 1374
<212> TYPE: DNA
<213> ORGANISM: Unknown
<220> FEATURE:
<223> OTHER INFORMATION: Pseudoalteromonas peptidolytica SNC 130

<400> SEQUENCE: 1
catgcagtcg agcggtaaca tttctagctt gctagaagat gacgagcggc ggacgggtga      60
gtaatgcttg ggaacatgcc ttgaggtggg ggacaaccat tggaaacgat ggctaatacc     120
gcataatgtc tacggaccaa aggggcttc ggctctcgcc tttagattgg cccaagtggg     180
attagctagt tggtgaggta agggctcacc aaggcgacga tccctagctg gtttgagagg     240
atgatcagcc acactggaac tgagacacgg tccagactcc tacgggaggc agcagtgggg     300
aatattgcac aatgggcgca agcctgatgc agccatgccg cgtgtgtgaa gaaggcctta     360
gggttgtaaa gcactttcag tcaggaggaa aggttagtag ttaatacctg ctagctgtga     420
cgttactgac agaagaagca ccggctaact ccgtgccagc agccgcggta atacggaggg     480
tgcgagcgtt aatcggaatt actgggcgta aagcgtacgc aggcggtttg ttaagcgaga     540
tgtgaaagcc ccgggcttaa cctgggaact gcatttcgaa ctggcaaact agagtgtgat     600
agagggtggt agaatttcag gtgtagcggt gaaatgcgta gagatctgaa ggaataccga     660
tggcgaaggc agccacctgg gtcaacactg acgctcatgt acgaaagcgt ggggagcaaa     720
caggattaga taccctggta gtccacgccg taaacgatgt ctactaggag ctgggtcttt     780
cggacaactt ttccaaagct aacgcattaa gtagaccgcc tggggagtac ggccgcaagg     840
ttaaaactca aatgaattga cggggccccg cacaagcggt ggagcatgtg gtttaattcg     900
atgcaacgcg aagaacctta cctacacttg acatacagag aacttaccag agatggtttg     960
gtgccttcgg gaactctgat acaggtgctg catggctgtc gtcagctcgt gttgtgagat    1020
gttgggttaa gtcccgcaac gagcgcaacc cctatcctta gttgccagcg attcggtcgg    1080
gaactctaag gagactgccg gtgataaacc ggaggaaggt ggggacgacg tcaagtcatc    1140
atggccctta cgtgtagggc tacacacgtg ctacaatggc aggtacagag agcagcgagc    1200
tagcgatagt gagcgaatcc cttaaagcct gtcgtagtcc ggattggagt ctgcaactcg    1260
actccatgaa gtcggaatcg ctagtaatcg cgaatcagaa tgtcgcggtg aatacgttcc    1320
cgggccttgt acacaccgcc cgtcacacca tgggagtggg ttgctccaga agtg          1374

<210> SEQ ID NO 2
<211> LENGTH: 20
<212> TYPE: DNA
<213> ORGANISM: Artificial Sequence
<220> FEATURE:
<223> OTHER INFORMATION: 27F primer

<400> SEQUENCE: 2
agagtttgat cmtggctcag                                                   20
```

```
<210> SEQ ID NO 3
<211> LENGTH: 22
<212> TYPE: DNA
<213> ORGANISM: Artificial Sequence
<220> FEATURE:
<223> OTHER INFORMATION: 1492R primer

<400> SEQUENCE: 3
tacggytacc ttgttacgac tt                                              22
```

SKIN WHITENING COMPOSITION COMPRISING CULTURED PRODUCT OF PSEUDOALTEROMONAS PEPTIDOLYTICA OR EXTRACT THEREOF

CROSS REFERENCE TO RELATED APPLICATIONS

This application is a National Stage of International Application No. PCT/KR2018/010834, filed Sep. 14, 2018, claiming priority to Korean Patent Application No. 10-2017-0118927, filed Sep. 15, 2017.

TECHNICAL FIELD

Disclosed in the present specification is a skin whitening composition containing a *Pseudoalteromonas peptidolytica* strain, a lysate thereof, a cultured product thereof, or an extract of the strain, lysate or cultured product as an active ingredient.

BACKGROUND ART

Human skin color is determined by carotene, the amount of melanin, hemoglobin, etc. Among them, melanin plays the most important role. Melanin is a pigment responsible for skin color and the color of hair and eye and plays an important role of protecting human skin. However, excessive production of melanin in the skin due to external environments such as excessive exposure to UV, air pollution, stress, etc. causes skin darkening, liver spots, freckles, etc. UV radiation is the major factor that induces melanin overproduction through promotion of the activity of melanin-producing melanocytes, promotion of the secretion of melanin biosynthesis-stimulating hormones, promotion of melanin oxidation, promotion of tyrosinase activity, etc. The most recognizable feature of the melanin production mechanism is that the enzyme called tyrosinase is involved. Therefore, skin whitening effect may be expected if the melanin production is prevented by inhibiting the activity of tyrosinase.

*Pseudoalteromonas* is a genus of marine bacteria known to form biofilms. However, its skin whitening effect has not been reported at all. The *Pseudoalteromonas peptidolytica* strain was discovered in 2000 by Japanese researchers but nothing is known about its use.

REFERENCES OF RELATED ART

Patent Documents

Korean Patent Registration Publication No. 10-0812922.

DISCLOSURE

Technical Problem

In an aspect, the present specification is directed to providing a new use of a *Pseudoalteromonas peptidolytica* strain.

In another aspect, the present specification is directed to providing a *Pseudoalteromonas peptidolytica* SNC 130 strain having superior skin whitening activity.

Technical Solution

In another aspect, the present specification provides a skin whitening composition containing: a *Pseudoalteromonas peptidolytica* strain; a lysate thereof; a cultured product thereof; or an extract of the strain, lysate or cultured product as an active ingredient.

In an exemplary embodiment, the strain may be *Pseudoalteromonas peptidolytica* SNC 130 having an accession number of KCCM12050P.

In an exemplary embodiment, the strain may have 16S rDNA including a base sequence of SEQ ID NO 1.

In an exemplary embodiment, the cultured product may be cultured in a culture medium including one or more selected from a group consisting of starch, yeast extract, peptone and sea salt.

In an exemplary embodiment, the extract may be an ethyl acetate fraction.

In an exemplary embodiment, the active ingredient may be contained in an amount of 0.001-30 wt % based on the total weight of the composition.

In an exemplary embodiment, the composition may inhibit melanin production or tyrosinase activity.

In an exemplary embodiment, the composition may be a cosmetic composition.

In another aspect, the present specification provides a *Pseudoalteromonas peptidolytica* SNC 130 strain having an accession number of KCCM12050P, having skin whitening function.

In an exemplary embodiment, the strain may be isolated from seaweed.

Advantageous Effects

In an aspect, the present specification provides an environment-friendly skin whitening ingredient.

In another aspect, the present specification provides a use of a *Pseudoalteromonas peptidolytica* strain for skin whitening. The strain has an effect of inhibiting melanin production in melanocytes and inhibiting the enzyme activity of producing the melanin pigment.

In another aspect, the present specification provides a *Pseudoalteromonas peptidolytica* SNC 130 strain having superior skin whitening activity.

BRIEF DESCRIPTION OF DRAWINGS

FIG. 1 shows the 16s rDNA sequence (SEQ ID NO 1) of a *Pseudoalteromonas peptidolytica* SNC 130 strain having an accession number of KCCM12050P according to the present specification.

FIG. 2 shows the skin cell safety of a *Pseudoalteromonas peptidolytica* strain according to an exemplary embodiment of the present specification.

FIG. 3 shows the melanin production inhibiting effect of a *Pseudoalteromonas peptidolytica* strain according to an exemplary embodiment of the present specification.

FIG. 4 shows the effect of inhibiting the activity of a melanin-producing enzyme of a *Pseudoalteromonas peptidolytica* strain according to an exemplary embodiment of the present specification.

BEST MODE

Hereinafter, the present disclosure is described in detail.

In an aspect, the present specification provides a skin whitening composition containing: a strain in the genus *Pseudoalteromonas;* a lysate thereof; a cultured product thereof; or an extract of the strain, lysate or cultured product as an active ingredient.

In another aspect, the present specification provides a method for enhancing skin whitening, which includes administering a strain in the genus *Pseudoalteromonas*, a lysate thereof, a cultured product thereof, or an extract of the strain, lysate or cultured product of an amount effective for enhancing skin whitening to a subject in need thereof.

In another aspect, the present specification provides a strain in the genus *Pseudoalteromonas*, a lysate thereof, a cultured product thereof, or an extract of the strain, lysate or cultured product for enhancing skin whitening of a subject.

In another aspect, the present specification provides a non-therapeutic use of a strain in the genus *Pseudoalteromonas*, a lysate thereof, a cultured product thereof, or an extract of the strain, lysate or cultured product for enhancing skin whitening of a subject.

In another aspect, the present specification provides a use of a strain in the genus *Pseudoalteromonas*, a lysate thereof, a cultured product thereof, or an extract of the strain, lysate or cultured product for preparing a composition for enhancing skin whitening.

In another aspect, the present specification provides a *Pseudoalteromonas peptidolytica* SNC 130 strain having an accession number of KCCM12050P.

In an exemplary embodiment, the strain in the genus *Pseudoalteromonas*, the lysate thereof, the cultured product thereof, or the extract of the strain, lysate or cultured product may be administered or applied or spreaded to a subject in the form of a composition, e.g., a composition for external application to skin or a cosmetic composition.

In an exemplary embodiment, the strain in the genus *Pseudoalteromonas*, the lysate thereof, the cultured product thereof, or the extract of the strain, lysate or cultured product may be administered to the skin of a subject.

In an exemplary embodiment, the strain in the genus *Pseudoalteromonas* may be a *Pseudoalteromonas peptidolytica* strain.

Specifically, in an exemplary embodiment, the strain may be preferred to be *Pseudoalteromonas peptidolytica* SNC 130 having an accession number of KCCM12050P.

In an exemplary embodiment, the strain may have 16S rDNA including the base sequence of SEQ ID NO 1.

In an exemplary embodiment, the *Pseudoalteromonas peptidolytica* SNC 130 strain may have skin whitening function.

In the present specification, the "active ingredient" refers to an ingredient capable of affording a desired activity either alone or together with a carrier, etc. which has no activity in itself.

Microbial resources are advantageous in that they can be utilized as renewable resources unlike petroleum, water, etc.

In an exemplary embodiment, the strain may be prepared as follows. After culturing the strain and centrifuging the culture medium, followed by washing with sterilized physiological saline and suspending in a solvent, e.g., sterilized milk, it may be prepared into freeze-dried powder.

The lysate of the strain may refer to a product obtained by lysing the strain itself either chemically or by applying physical force.

The cultured product of the strain may refer to a material comprising some or all substances included in the culture medium in which the strain was cultured, regardless of the type of the cultured product. For example, it may refer to a material including a metabolite or a secreted product resulting from the culturing of the strain, or a lysate thereof, and the strain itself may also be included in the cultured product.

In an exemplary embodiment, the cultured product may be cultured in a culture medium including one or more selected from a group consisting of starch, yeast extract, peptone and sea salt.

The extract may refer to a product obtained by extracting, isolating or fractionating the strain itself, a lysate of the strain, a cultured product of the strain or a mixture thereof, regardless of extraction method, extraction solvent, extracted ingredients or type of the extract. The term is used in a broad concept, including any substance that can be obtained through processing or treating after the extraction.

In an exemplary embodiment, the extract may be preferred to be an ethyl acetate fraction of a culture of *Pseudoalteromonas peptidolytica*.

In an exemplary embodiment, the strain in the genus *Pseudoalteromonas*, the lysate thereof, the cultured product thereof, or the extract of the strain, lysate or cultured product may be contained in an amount of 0.001-30 wt % based on the total weight of the composition. In another aspect, the strain in the genus *Pseudoalteromonas*, the lysate thereof, the cultured product thereof, or the extract of the strain, lysate or cultured product may be contained in an amount of 0.001 wt % or more, 0.01 wt % or more, 0.1 wt % or more, 0.5 wt % or more, 1 wt % or more, 1.5 wt % or more or 2 wt % or more, and 30 wt % or less, 25 wt % or less, 20 wt % or less, 15 wt % or less, 10 wt % or less or 5 wt % or less, based on the total weight of the composition.

The strain in the genus *Pseudoalteromonas*, the lysate thereof, the cultured product thereof, the extract of the strain, lysate or cultured product, or the skin whitening composition containing the same according to the present disclosure has an effect of preventing, improving and/or treating a symptom or a disease caused by melanin overproduction by effectively inhibiting melanin production.

In an exemplary embodiment, the symptom or disease caused by melanin overproduction may be one or more selected from a group consisting of liver spots, freckles, age spots, blemish, epidermal melanocytic lesions, café au lait macules, Becker's nevus, nevus spilus, lentigines, dermal melanocytic lesions, Mongolian spot, nevus of Ota, acquired bilateral nevus of Ota-like macules, nevus of Ito, blue nevus, melanocytic nevus, junctional nevus, compound nevus, intradermal nevus, halo nevus, congenital nevocytic nevus, Spitz nevus, dysplastic nevus, melanoma, lentigo maligna melanoma, superficial spreading melanoma, acral lentiginous melanoma, nodular melanoma, pigmented basal cell carcinoma, pigmented dermatofibromas, dermoid cyst, pigmented keloid and pigmented keratoacanthomas.

In an exemplary embodiment, the strain in the genus *Pseudoalteromonas*, the lysate thereof, the cultured product thereof, the extract of the strain, lysate or cultured product, or the composition containing the same may prevent, improve and/or treat skin pigmentation.

In an exemplary embodiment, the strain in the genus *Pseudoalteromonas*, the lysate thereof, the cultured product thereof, the extract of the strain, lysate or cultured product, or the composition containing the same may prevent, improve and/or treat one or more skin pigmentation selected from a group consisting of liver spots, freckles, dark spots, nevus, melanoma, drug-induced pigmentation, inflammation-induced pigmentation and dermatitis-induced pigmentation, which occurs topically in skin due to increased melanin production.

In an exemplary embodiment, the composition may be a composition for external application to skin.

In an exemplary embodiment, the composition for external application to skin may further contain a pharmaceutical adjuvant such as antiseptic, a stabilizer, a wetting agent, an emulsification promoter, a salt and/or a buffer for controlling osmotic pressure, etc. and other therapeutically useful substances in addition to the active ingredient according to the present specification, and may be formulated into various forms for parenteral application according to common methods.

In an exemplary embodiment, the formulation for parenteral application may be for transdermal application. For example, the formulation may be an injection, an ointment, a lotion, a gel, a cream, a spray, a suspension, an emulsion, a patch, etc., although not being limited thereto.

In an exemplary embodiment, the composition for external application to skin may be a topical medication having pharmaceutical use for a disease related with melanin production.

In an exemplary embodiment, the composition may be a cosmetic composition.

In an exemplary embodiment, the cosmetic composition may further contain functional additives and ingredients contained in general cosmetic compositions in addition to the active ingredient according to the present specification. The functional additive may be an ingredient selected from a group consisting of a water-soluble vitamin, an oil-soluble vitamin, a polypeptide, a polysaccharide, a sphingolipid and a seaweed extract. In addition, an ingredient such as an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation stimulant, a cooling agent, an antiperspirant, purified water, etc. may be further contained.

The formulation of the cosmetic composition is not particularly limited and may be selected adequately depending on purposes. For example, the cosmetic composition may be prepared into one or more formulation selected from a group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

In an exemplary embodiment, when the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

In an exemplary embodiment, when the formulation of the present disclosure is a powder or a spray, lactose, talc, silica, aluminum hydroxide, calcium silicate or polyamide powder may be used as a carrier ingredient. In particular, when the formulation is a spray, it may further contain a propellant such as chlorofluorohydrocarbon, propane/butane or dimethyl ether.

In an exemplary embodiment, when the formulation of the present disclosure is a solution or an emulsion, a solvent, a solubilizer or an emulsifier, e.g., water, ethanol, isopropanol, ethyl carbonate, ethyl acetate, benzyl alcohol, benzyl benzoate, propylene glycol, 1,3-butylene glycol, a glycerol aliphatic ester, polyethylene glycol or a fatty acid ester of sorbitan may be used as a carrier ingredient.

In an exemplary embodiment, when the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

In an exemplary embodiment, when the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an amidoalkyl betaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

[Mode for Invention]

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Isolation and Identification of Strain

Harvested seaweed was heat-treated at 60° C. for 10 minutes to remove Gram-negative bacteria. Then, microorganisms existing on the surface of the seaweed were isolated using physiological saline (0.85% NaCl). The physiological saline solution was diluted 10-fold and 100-fold using physiological saline and then inoculated to an isolation medium (10 g/L starch, 4 g/L yeast extract, 2 g/L peptone, 16 g/L agar, 34.75 g/L sea salt) supplemented with an antibiotic (chloramphenicol 20 µg/mL). The inoculated medium was incubated at 27° C. for 7-30 days, and a single strain forming a colony was isolated finally by subculturing for 2-4 passages.

The isolated strain was identified through 16S rRNA base sequencing using 27F (5'- AGAGTTT-GATCMTGGCTCAG-3', SEQ ID NO 2) and 1492R (5'-TACGGYTACCTTGTTACGACTT-3', SEQ ID NO 3) primers. As a result of Gene Bank search, the isolated strain was confirmed to have 99.8% similarity to *Pseudoalteromonas peptidolytica* strain NBRC 101021 and named as *Pseudoalteromonas peptidolytica* SNC 130. The strain was deposited under the Budapest Treaty on the International Recognition of the Deposit of Microorganisms for the Purpose of Patent Procedure on Jun. 27, 2017 in the Korean Culture Center of Microorganisms (KCCM) of Yurim B/D 45, Hongjenae-2ga-gil, Seodaemun-gu, Seoul, Republic of Korea and was given the accession number KCCM12050P.

EXAMPLE 2

Preparation of Cultured Product and Extract of *Pseudoalteromonas peptidolytica* Strain The *Pseudoalteromonas peptidolytica* SNC 130 strain identified in Example 1 was inoculated to a culture medium (10 g/L starch, 2 g/L yeast extract, 4 g/L peptone, 34.75 g/L sea salt) and a culture of the *Pseudoalteromonas peptidolytica* strain was obtained by culturing the same at 27° C. and 120 rpm for 7 days.

The obtained culture of the *Pseudoalteromonas peptidolytica* strain was added to ethyl acetate of the same volume and an ethyl acetate fraction was obtained by conducting reaction. Then, an extract was obtained by removing the ethyl acetate using an evaporator.

EXAMPLE 3

Confirmation of Skin Cell Safety of Pseudoalteromonas peptidolytica Strain

Experiment was conducted as follows to investigate whether the Pseudoalteromonas peptidolytica strain is safe for skin cells.

Specifically, after dissolving the extract of the Pseudoalteromonas peptidolytica strain isolated from the seaweed obtained in Example 2 in DMSO (dimethyl sulfoxide) and treating skin cells (HaCaT) with the extract, the effect on the activity of the cells was investigated. After seeding 100 μL of the skin cells onto a 96-well cell culture plate at a concentration of $2 \times 10^5$ cells/mL and culturing for 24 hours, followed by treating with the extract of the Pseudoalteromonas peptidolyticastrain at concentrations of 10-100 μg/mL, the cells were cultured further for 24 hours. The experiment was repeated 3 times for the respective concentrations. The cell activity was compared by MTT assay and was represented relative to the activity of the untreated group as 100%.

As a result, the Pseudoalteromonas peptidolytica strain isolated from the seaweed was confirmed to be safe the skin cells since they had no effect on the growth of the skin cells (see FIG. 2).

EXAMPLE 4

Confirmation of Skin Whitening Effect of Pseudoalteromonas peptidolytica Strain The skin whitening effect of the Pseudoalteromonas peptidolytica strain was tested as follows.

Specifically, the skin whitening effect was evaluated by treating melanocytes (B16 melanoma cells) with the extract of the Pseudoalteromonas peptidolytica strain isolated from the seaweed obtained in Example 2. The melanocytes seeded onto a 24-well cell culture plate at a concentration of $4 \times 10^4$ cells/well and cultured for 24 hours were used for the experiment. The cells were treated with 1 μM α-MSH (α-melanocyte-stimulating hormone) to induce melanin production and at the same time with the extract of the Pseudoalteromonas peptidolytica strain at concentrations of 10-50 μg/mL. The experiment was repeated 3 times for the respective concentrations. After culturing further for 72 hours, absorbance was measured at 405 nm in order to compare the melanin content in the culture medium. The degree of melanin production of the groups treated with the extract was represented relative to the absorbance of the melanin production-induced group as 100%.

In addition, tyrosinase activity was compared by reacting mushroom tyrosinase with the extract for a predetermined time using L-tyrosine as a substrate and then measuring absorbance at 475 nm. After adding tyrosinase to a buffer (0.1 M potassium phosphate buffer) at a concentration of 2 units/μL, the substrate concentration was adjusted to 0.3 mg/mL. Then, after adding the extract at concentrations of 10-50 μg/mL and 100 μL of L-DOPA, absorbance was measured immediately at 475 nm. Then, after conducting reaction at 37° C. for 10 minutes, absorbance was measured again. The difference in the absorbance of the extract-treated groups was represented relative to the difference in the absorbance of the untreated group as 100%.

As a result, it was confirmed that the extract inhibited the melanin production in the melanocytes in a concentration-dependent manner (see FIG. 3), which was due to the inhibited activity of the melanin-producing enzyme tyrosinase (see FIG. 4). Accordingly, it was confirmed that the Pseudoalteromonas peptidolytica strain has skin whitening effect.

Hereinafter, formulation examples of the composition according to an aspect of the present disclosure will be described. However, the following formulation examples are for illustrative purposes only and the scope of the present disclosure is not limited by them.

FORMULATION EXAMPLE 1

Softening Lotion

A softening lotion was prepared according to a common method by mixing 0.01 wt % of the Pseudoalteromonas peptidolytica culture of Example 2, 3 wt % of glycerin, 2 wt % of butylene glycol, 2 wt % of propylene glycol, 0.1 wt % of a carboxyvinyl polymer, 10 wt % of ethanol, 0.1 wt % of triethanolamine, an antiseptic as balance, a trace amount of a colorant, a trace amount of a fragrance and a trace amount of purified water.

FORMULATION EXAMPLE 2

Nourishing Lotion

A nourishing lotion was prepared according to a common method by mixing 0.01 wt % of the Pseudoalteromonas peptidolytica culture of Example 2, 4 wt % of beeswax, 1.5 wt % of polysorbate 60, 0.5 wt % of sorbitan sesquioleate, 5 wt % of liquid paraffin, 5 wt % of squalane, 5 wt % of caprylic/capric triglyceride, 3 wt % of glycerin, 3 wt % of butylene glycol, 3 wt % of propylene glycol, 0.1 wt % of a carboxyvinyl polymer, 0.2 wt % of triethanolamine, an antiseptic as balance, a trace amount of a colorant, a trace amount of a fragrance and a trace amount of purified water.

FORMULATION EXAMPLE 3

Nourishing Cream

A nourishing cream was prepared according to a common method by mixing 0.01 wt % of the Pseudoalteromonas peptidolytica culture of Example 2, 10 wt % of beeswax, 1.5 wt % of polysorbate 60, 0.5 wt % of sorbitan sesquioleate, 10 wt % of liquid paraffin, 5 wt % of squalane, 5 wt % of caprylic/capric triglyceride, 5 wt % of glycerin, 3 wt % of butylene glycol, 3 wt % of propylene glycol, 0.2 wt % of triethanolamine, an antiseptic as balance, a trace amount of a colorant, a trace amount of fragrance and a trace amount of purified water.

FORMULATION EXAMPLE 4

Pack

A pack was prepared according to a common method by mixing 0.01 wt % of the Pseudoalteromonas peptidolytica culture of Example 2, 13 wt % of polyvinyl alcohol, 0.2 wt % of sodium carboxymethyl cellulose, 0.1 wt % of allantoin, 5 wt % of ethanol, 0.3 wt % of nonyl phenyl ether, an antiseptic as balance, a trace amount of a colorant, a trace amount of fragrance and a trace amount of purified water.

Although the particular embodiments of the present disclosure have been described in detail, it will be apparent to those of ordinary skill in the art that they are only specific exemplary embodiments and the scope of the present disclosure is not limited by them. Accordingly, the substantial scope of the present disclosure will be defined by the appended claims and their equivalents.

[Accession Number]

Depository authority: Korean Culture Center of Microorganisms
Accession number: KCCM12050P
Date of deposition: Jun. 27, 2017

The invention claimed is:

1. A method for enhancing skin whitening, which comprises administering to a subject in need thereof an effective amount of a composition comprising *Pseudoalteromonas peptidolytica* strain no. SNC 130; a lysate thereof; a cultured product thereof; or an extract thereof.

2. The method for enhancing skin whitening according to claim 1, wherein the strain has a 16S rRNA comprising the polynucleotide sequence of SEQ ID NO 1.

3. The method for enhancing skin whitening according to claim 1, wherein the cultured product is a product of culturing the *Pseudoalteromonas peptidolytica* strain no. SNC 130 in a culture medium comprising one or more components selected from the group consisting of starch, yeast extract, peptone and sea salt.

4. The method for enhancing skin whitening according to claim 1, wherein the extract is an ethyl acetate fraction.

5. The method for enhancing skin whitening according to claim 1, wherein the composition comprises 0.001-30% by weight of the *Pseudoalteromonas peptidolytica* strain, the lysate thereof, the cultured product thereof, or the extract thereof.

6. The method for enhancing skin whitening according to claim 1, wherein the composition inhibits melanin production or tyrosinase activity.

7. The method for enhancing skin whitening according to claim 1, wherein the composition is a cosmetic composition.

* * * * *